United States Patent
Roversi

(10) Patent No.: US 7,056,377 B2
(45) Date of Patent: Jun. 6, 2006

(54) USE OF AN ACETYLATED PRE-GELLED STARCH WITH A HIGH CONTENT OF AMYLOSE

(75) Inventor: Francesco Roversi, Lugano (CH)

(73) Assignee: F.T. Holdings S.A., Luxembourg (LU)

( * ) Notice: Subject to any disclaimer, the term of this patent is extended or adjusted under 35 U.S.C. 154(b) by 0 days.

(21) Appl. No.: 10/311,794

(22) PCT Filed: Jan. 26, 2001

(86) PCT No.: PCT/EP01/00871

§ 371 (c)(1),
(2), (4) Date: Nov. 10, 2003

(87) PCT Pub. No.: WO02/00205

PCT Pub. Date: Jan. 3, 2002

(65) Prior Publication Data

US 2004/0069300 A1   Apr. 15, 2004

(30) Foreign Application Priority Data

Jun. 23, 2000   (IT) .......................... MI2000A1421

(51) Int. Cl.
*C09D 103/06* (2006.01)
*A61K 9/14* (2006.01)
*A61K 9/34* (2006.01)
*A61K 9/36* (2006.01)
*A61K 9/48* (2006.01)

(52) U.S. Cl. ............... 106/207.1; 106/207.5; 106/205.71; 536/48; 424/463; 424/479; 424/493; 426/103; 426/302; 427/212; 428/403; 524/51

(58) Field of Classification Search ............ 106/207.1, 106/207.5, 205.71; 536/48; 424/463, 479, 424/493; 426/103, 302; 427/212; 428/403; 524/51

See application file for complete search history.

(56) References Cited

U.S. PATENT DOCUMENTS

| | | | |
|---|---|---|---|
| 3,622,677 A * | 11/1971 | Short et al. ................. | 514/778 |
| 3,751,268 A | 8/1973 | Van Patten et al. | |
| 4,026,986 A | 5/1977 | Christen | |
| 4,487,786 A | 12/1984 | Junge | |
| 4,738,724 A | 4/1988 | Wittwer et al. | |
| 5,281,276 A | 1/1994 | Chiu | |
| 5,321,132 A * | 6/1994 | Billmers et al. ............. | 536/48 |
| 5,554,385 A | 9/1996 | Stroud | |
| 5,945,468 A * | 8/1999 | Atkinson et al. ............ | 524/51 |
| 6,184,213 B1 | 2/2001 | Lefevre et al. | |

FOREIGN PATENT DOCUMENTS

GB   810306   3/1959

* cited by examiner

*Primary Examiner*—David Brunsman
(74) *Attorney, Agent, or Firm*—Abelman, Frayne & Schwab

(57) ABSTRACT

A starch with a high content in amylose, obtained through a process comprising acetylation and pre-gellation, can provide useful coatings in food, drug, cosmetic and dietetic fields, both for humans and animals, and also in agriculture.

21 Claims, No Drawings

USE OF AN ACETYLATED PRE-GELLED STARCH WITH A HIGH CONTENT OF AMYLOSE

This application is a 371 filing of PCT/EP01/00871, filed 26 Jan. 2001.

FIELD OF THE INVENTION

A chemically modified starch with a high content in amylose, obtained through a pre-gellation process, allows to obtain films endowed with a suitable mechanical resistance for the production of capsules and coatings for solid formulations used in drug, cosmetic, food and dietetic fields, and also in agriculture.

STATE OF THE ART

There are several different types of starch depending on the original variety, for instance maize, rice, potato and tapioca, and on the different percentage of amylopectin and amylose. Starches having a high content of amylose (hereinafter HAS) show at least 50% of said substance on their total weight. They can come from particular vegetal hybrids or they are prepared by enriching with amylose starches with a poor content of said component. Amylose attributes consistence properties heat stability, water resistance and adhesiveness, so that starches having a high content of amylose (hereinafter HAS) shows undoubtful advantages if compared with other starches. Examples of HAS are those commercially available with the trademarks Eurylon™, Amylon™, Exylon™, and Nabond™.

HAS are used either as such or modified through various physical or chemical processes. One of the physical processes is pre-gellation, in which starch undergoes a heat treatment in the presence of water, thus losing its granular form and becoming water soluble at low temperatures. Among the chemical processes we can quote esterification and etherification, for instance acetylation.

HAS are used in several fields such as food and pharmaceutical industry.

As far as its uses in food field are concerned we can mention for instance U.S. Pat. No. 3,751,268 (belonging to American Maize-Products Company), which discloses the use a non-modified non-gelled HAS for coating foods to be fried in deep oil. Similarly, U.S. Pat. No. 4,487,786 (belonging to Lamb-Weston Inc.) claims a method for coating frozen foods by means of a mixture comprising a HAS, wheat flour and an edible acid.

In the pharmaceutical field they are used for several aims. For instance the patent application EP 0 964 000 (belonging to Roquette Frères) discloses a diluting and disintegrating composition containing a HAS, preferably Eurylon™ included in a pre-gelled starch matrix, which can be used to produce solid forms such as powders or tablets.

U.S. Pat. No. 5,554,385 (in the name of R.P. Scherer Corporation) relates to soft gelatin capsules in which a certain percentage of gelatin is replaced by a HAS. These capsules show a lower tendency to stick one another, they are more resistant and have a better appearance.

U.S. Pat. No. 4,026,986 (in the name of The Dow Chemical Company) relates on the other hand to capsules which can be wholly constituted by a hydroxyalkylated HAS. These capsule show the advantage of being more uniform, more stable to water and high temperatures during the manufacturing process, and cheaper.

GB 810,306 (in the name of The Upjohn Company) claims among other things an amylose diester, preferably an acetate phthalate amylose, which can be used as a coating for gastro-resistant pharmaceutical preparations. This kind of coating shows nevertheless a disadvantage due to the permanence of possible residues of phthalic acid in the finished product which should absolutely be removed through a quite complex process consisting of 4 re-suspensions in deionized water at room temperature, followed by a treatment with boiling water.

U.S. Pat. No. 4,738,724 (in the name of Warner-Lambert Company) claims capsules for pharmaceutical use made of a starch/water mixture. The manufacturing process for these capsules is exceedingly complex and is not regarded as industrially convenient.

U.S. Pat. No. 5,281,276 (belonging to National Starch and Chemical Investment Holding Corp.) describes a method for obtaining a starch which is resistant to amylase, i.e. the enzyme hydrolyzing starch in the intestine. This method provides for the gellation of a starch having a content of amylose above 40% and then its treatment with an enzyme which can "de-branch" starch chains.

The coating of pharmaceutical, food, dietetic and cosmetic forms for humans and animals and the coating of seeds in agriculture has several functions. Among the most important ones there is in the pharmac utical industry the need to cover the unpleasant taste of some active principles or compositions, the possibility to protect the formulation from room humidity for example food industry and in agriculture in the food and pharmaceutical industry, humidity, which can cause degradation phenomena, in the pharmaceutical and food industry the need is felt for a gastro-resistance, so that the drug or nourishing agent reaches intact the intestine to be absorbed.

In the food field this problem has a particular relevance, since for legislative reasons it is not possible to use acrylic and methacrylic polymers, such as Eudragit™, commonly used in the pharmaceutical field. The only material which can be useful to the aforesaid purposes and which can legally be used is shellac, which nevertheless shows problems related to lot, weight and structure uniformity, and also requires solvents different from water for its processing and application.

Beyond these specific problems the need for non-toxic materials which are well tolerated by organisms is always present in both sectors. For instance some users find difficulty in digesting coatings based on gelatin, and in addition more and more people require and prefer pharmaceutical and food/dietetic preparations containing as much as possible of natural products or products of natural origin.

SUMMARY OF THE INVENTION

It has now been surprisingly found that an acetylated pre-gelled starch having a high content of amylose allows to produce capsules or coatings for solid formulations with reduced costs which are humidity- and light-resistant in some cases, gastro-resistant, which cover unpleasant tastes or smells, or In same case which are slow-release, by operating in an aqueous solvent.

Therefore, the present invention relates to the use of a pre-gelled acetylated starch with a high content of amylose for the production of capsules or coatings for solid formulations in drug, cosmetic, food and dietetic fields, both for humans and for animals and in agriculture for coating seeds.

DESCRIPTION OF THE INVENTION

Scope of the present invention is the use of an acetylated pre-gelled starch having a high content of amylose for the manufacturing of capsules and coatings for solid formulations in drug, cosmetic, food and dietetic fields, both for humans and animals and also for coating seeds in agriculture.

The starch according to the present invention can be high amylose starch which can be found in nature from various sources, such as maize, potato, rice, wheat, sorghum, tapioca, etc., or which can be obtained by enriching with amylose any of the commercially available starches. Maize starch is preferred for the aims of the present invention.

Preferably, the starch according to the present invention is naturally or artificially enriched with above 50% by weight amylose. More preferably, the starch according to the present invention is a starch naturally containing amylose in a percentage equal to or above 50% by weight. More preferably for the aims of the present invention, a starch containing more than 90% by weight of amylose Is used.

The starch according to the present invention can be used alone or in combination with plasticizers and/or lubricants. Plasticizers can be selected from the group comprising sorbitol, glycerol, triethylcitrate, polysorbate, carnauba wax, PEG, preferably 6000 and mixtures thereof. Lubricants can be selected from the group comprising polyvinyl pyrrolidone, glycerol monostearate, colloidal silica, kaolin, titanium dioxide, magnesium stearate, alginates, talc and mixtures thereof. Talc is preferably used.

Preferably, starch compositions according to the present invention contain one or more plasticizers in amounts of 10–50% by weight referred to the starch weight, preferably 10%; one or more lubricants in amounts of 20–70% by weight referred to the starch weight, preferably 50%.

The compositions according to the present invention can also contain agents modulating the capacity of the capsule or of the coating to dissolve in given times or at given pH values, for example agents giving gastro-resistance selected from the group comprising acacia, shellac, cellulose and mixtures thereof. These are contained in amounts of 10 to 70% by weight on starch weight. Moreover, said compositions can contain other excipients such as for instance dyers.

The starch used for the aims of the present inventions is obtained from a maize starch with a high content of amylose, i.e. a content of amylose above 50% by weight. This starch is first acetylated using methods known to the person skilled in the art, for instance as described in *Starch*, Whistler, Bemiller and Pascal eds., Academic Press, (1984), page 332 and ff. Acetylation is preferably carried out with acetic anhydride, so as to obtain a percentage of acetylic groups higher than 0.5% by weight, but lower than 2.5% by weight. The starch thus modified then undergoes a pre-gellation/baking stage according to methods known to the people skilled in the art. In particular, acetylated starch is dispersed in an aqueous solution which is then poured onto a rotating drum heated at a temperature between 100° C. and 130° C., operating at pressures between 2 and 3 bar, so that on touching the roll surface the dispersion "explodes" with subsequent water evaporation in 30 seconds to 3 minutes. A gel layer containing the modified starch is thus deposited onto the rotating drum surface. This gel, usually having a humidity percentage varying from 5 to 10% by weight, solidifies and is removed by scraping.

The acetylated pre-gelled HAS is for example also available on the market for example with the trade name acetylated Eurylon™ G.

Acetylated pre-gelled starch is used to coat tablets, capsules, pellets and microgranules or to prepare hard or soft capsules according to known methods. For instance tablets and capsules can be coated with the starch according to the present invention by film-coating in a tray. The coating of pellets and microgranules, on the contrary, is usually carried out by film-coating in a fluidized bed, spray drying, spray congealing, ultrasonic atomization, rotogranulation or spheronization.

For the manufacture of soft and hard capsules using the starch according to the present invention the methods to be followed are those commonly known in the field. See for instance U.S. Pat. No. 2,299,039 (belonging to Robert P. Scherer). Preferably, the coating procedure encompasses suspending in water the starch according to the present invention together with possible excipients at 50–60° C. with a solid concentration of 10 to 25% by weight and preferably 20% by weight. The modified starch according to the present invention can provide coatings with an excellent resistance, while maintaining at the same time an acceptable viscosity degree enabling the processing thereof.

The starch according to the present invention allows to obtain coatings which can be protective from humidity, coatings, which are able to cover tastes or smells, which are in some cases even gastro-resistant and/or allowing a delayed release. Depending on the kind of coating to obtain a different amount of starch for surface unit to be coated is used in the covering processes.

In particular, in ord r to obtain a gastro-resistant coating it is necessary to use an amount of starch of 5 to 15 mg/cm$^2$, preferably 15 mg/cm$^2$, which can be reduced to an amount of 2 to 10 mg/cm$^2$, preferably 5 mg/cm$^2$, if the composition contains the above-mentioned agents giving gastro-resistance.

If the coating is used for protection from humidity and light such as in agriculture and food industry, for covering unpleasant tastes or smells or for slow-release, the amount of starch to be used is between 2 and 10 mg/cm$^2$, and preferably 5 mg/cm$^2$.

The invention will now be described in further detail thanks to the following examples.

EXAMPLE 1

Gastro-resistant Coating Formulation for Tablets

The following formulation can be used for coating with 5 mg/cm$^2$ of starch a lot of 8.3 kg of tablets, with a diameter of 7.5 mm, a height of 3.5 mm, each weighing 180 mg:

| | |
|---|---:|
| Modified starch | 395 g |
| Shellac | 197.5 g |
| Ammonium carbonate | 197.5 g |
| Talc | 197.5 g |
| Titanium dioxide | 66 g |
| Triethylcitrate | 19.75 g |
| Sorbitol | 19.75 g |
| Water | 3661.25 g |
| Total | 4576.5 g |

The solid content of the formulation is 20% w/w.

The total amount of starch in the formulation has been thus calculated:

Surface Area of a Tablet:

$$S=\pi(7.5\text{ mm}\cdot 3.5\text{ mm}+(7.5\text{ mm})^2/2)=170.74\text{ mm}^2$$

Amount of Starch for Each Tablet:

$$q=(5\text{ mg/cm}^2\cdot 170.74\cdot 10^{-2}\text{ cm}^2)=8.54\text{ mg}$$

Amount of Starch in the Whole Lot:

$$Q=8.54\text{ mg}\cdot 8.3\cdot 10^6\text{ mg}/180\text{ mg}=393.8\cdot 10^3\text{ mg}$$

EXAMPLE 2

Gastro-resistant Coating Formulation for Soft Gelatin Capsules

The following formulation can be used for coating a lot of soft gelatin capsules weighing 8 kg, with a length of 13 mm, a height of 7.5 mm, each weighing each 450 mg, with an amount of starch of 15 mg/cm$^2$:

| | |
|---|---:|
| Modified starch | 820 g |
| Talc | 410 g |
| Glycerol | 82 g |
| Water | 5248 g |
| Total | 6560 g |

The solid content of the formulation is 20%.

The total amount of starch in the formulation has been thus calculated:

Surface Area of a Capsule:

$$S=\pi(7.5\text{ mm}\cdot 13\text{ mm})=306.15\text{ mm}^2$$

Amount of Starch for Each Capsule:

$$q=15\text{ mg/cm}^2\cdot 306.15\cdot 10^{-2}\text{ cm}^2=46\text{ mg}$$

Amount of Starch in the Whole Lot:

$$Q=46\text{ mg}\cdot 8\cdot 10^6\text{ mg}/450\text{ mg}=818\cdot 10^3\text{ mg}$$

Gastro-resistance Test

The gastro-resistance of tablets and capsules coated with the formulations described in Examples 1 and 2 is evaluated according to the directives of F.U. X Ed. In particular, six tablets or capsules are introduced into a disintegrating device containing 0,1 N hydrochloric acid (pH=2) at 37° C. After 2 hours no disgregation can be observed. The tablets or capsules are then transferred to a buffer solution with pH=6.8. Under these conditions all tablets or capsules disintegrated in less than 10 minutes.

EXAMPLE 3

Protective Coating Formulation for Soft Gelatin Capsules or Tables

The following formulation can be used for coating with an amount of starch of 5 mg/cm$^2$ a lot of soft gelatin capsules weighing 8 kg, with a length of 13 mm, a height of 7.5 mm and weighing each 450 mg, so as to obtain protection from humidity and light:

| | |
|---|---:|
| Modified starch | 275 g |
| Talc | 137.5 g |
| Glycerol | 27.5 g |
| Water | 1760 g |
| Total | 2200 g |

The solid content of the formulation is 20%.

The total amount of starch in the formulation has been thus calculated:

Surface Area of a Capsule:

$$S=\pi(7.5\text{ mm}\cdot 13\text{ mm})=306.15\text{ mm}^2$$

Amount of Starch for Each Capsule:

$$q=5\text{ mg/cm}^2\cdot 306.15\cdot 10^{-2}\text{ cm}^2=15.3\text{ mg}$$

Amount of Starch in the Whole Lot:

$$Q=15.3\text{ mg}\cdot 8\cdot 10^6\text{ mg}/450\text{ mg}=272\cdot 10^3\text{ mg}$$

Humidity Resistance Test

The resistance to humidity of capsules coated with the formulation in Example 3 is evaluated. To this purpose 100 capsules are kept in a non-dehumidified ambient under non-controlled temperature conditions for a month. At the end of this period a visual inspection of the capsules is carried out, confirming the absence of any alteration.

Viscosity of a Suspension with 20% of Starch

The viscosity of a suspension containing 20% of modified starch is analyzed using a Brookfield Viscosimeter (DV-II model, probe no. 5, 20 rpm). The viscosity values obtained at different temperatures are listed in the table below:

| TEMPERATURE (° C.) | VISCOSITY (mPa · s) |
|---|---|
| 80 | 4500 |
| 70 | 5500 |
| 60 | 7000 |
| 50 | 10000 |

Viscosity of Formulations for Tablets or Capsules Coating

The Brookfield viscosity of the following formulations used for tablets or capsules coating is measured at 60° C. under the same operating conditions as in previous

| viscosity test: | |
|---|---:|
| a) formulation 1 | |
| Modified starch | 81 g |
| Neosorb P100 | 9 g |
| Water | 510 g |
| b) formulation 2 | |
| Modified starch | 81 g |
| Glycerol | 9 g |
| Water | 510 g |
| b) formulation 3 | |
| Modified starch | 87 g |
| Neosorb P100 | 3 g |
| Water | 510 g |

-continued viscosity test:

d) formulation 4

| | |
|---|---|
| Modified starch | 87 g |
| Glycerol | 3 g |
| Water | 510 g |

The viscosity values obtained for the various formulations are listed in the table below:

| FORMULATION | VISCOSITY (mPa · s) |
|---|---|
| 1 | 480 |
| 2 | 400 |
| 3 | 520 |
| 4 | 500 |

The invention claimed is:

1. A process for coating seeds or solid formulations to be used in drug, cosmetic, food and dietetic fields, both for humans and for animals comprising:
   a) preparing an aqueous suspension of an acetylated pre-gelled starch containing at least 50% by weight of amylose, said suspension optionally containing excipients; and,
   b) coating said solid formulations with the suspension prepared in step (a).

2. The process according to claim 1 wherein said acetylated pregelled starch shows a percentage of acetylic groups of 0.5 to 2.5% by weight.

3. The process according to claim 1, wherein the starch used in step (a) is maize starch.

4. The process according to claim 1, wherein the starch used in step (a) is synthetically enriched with amylose in a percentage higher than or equal to 50% by weight.

5. The process according to claim 1, wherein the starch used in step (a) naturally contains amylose in a percentage higher than or equal to 50% by weight.

6. The process according to claim 1, wherein said starch has a content of amylose higher than 90%.

7. The process according to claim 1, wherein the suspension obtained in step (a) contains as optional excipients plasticizers and/or lubricants.

8. The process according to claim 7, wherein said plasticizers are selected from the group consisting of sorbitol, glycerol, triethylcitrate, polysorbate, carnauba wax, PEG, and mixtures thereof.

9. The process according to claim 7, wherein said lubricants are selected from the group consisting of polyvinyl pyrrolidone, glycerol monostearate, colloidal silica, kaolin, titanium dioxide, magnesium stearate, alginates, talc and mixtures thereof.

10. The process according to claim 9 wherein said lubricant is talc.

11. The process according to claim 7, wherein said plasticizers are present in an amount of 10% to 50%, by weight, based on the starch weight.

12. The process according to claim 11, wherein said plasticizers are present in an amount of 10%, by weight, based on the starch weight.

13. The process according to claim 7, wherein said lubricants are present in an amount of 20% to 70%, by weight, based on the starch weight.

14. The process according to claim 13, wherein said lubricants are present in an amount of 50%, by weight, based on the starch weight.

15. The process according to claim 1, wherein the suspension prepared in step (a) contains as excipients agents providing gastroresistance.

16. The process according to claim 15, wherein said agents are selected from the group consisting of acacia, shellac cellulose and mixtures thereof.

17. The process according to claim 1 wherein step (a) is carried out at a temperature ranging from 50 to 60° C.

18. The process according to claim 17 wherein the suspension obtained in step (a) has a solid concentration of 20%, by weight.

19. The process according to claim 1, wherein the suspension obtained in step (a) has a solid concentration ranging from 10 to 25%, by weight.

20. The process according to claim 1, wherein when the solid formulation is a capsule or a tablet, the coating provided in step (b) is a film coating.

21. The process according to claim 1, wherein when the solid formulation is in the form of granules or pellets the coating in step (b) is realized with a technique selected from the group consisting of film coating, spray drying, spray congealing, spheronization, ultrasonic atomisation, and rotogranulation.

* * * * *